(12) United States Patent
Yaghoubi et al.

(10) Patent No.: US 12,180,305 B2
(45) Date of Patent: Dec. 31, 2024

(54) SYSTEMS AND METHODS FOR IMMOBILIZING A TARGET PROTEIN

(71) Applicant: UNIVERSITY OF SOUTH FLORIDA, Tampa, FL (US)

(72) Inventors: Houman Yaghoubi, Tampa, FL (US); Arash Takshi, Tampa, FL (US); John Thomas Beatty, Vancouver (CA)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 387 days.

(21) Appl. No.: 17/498,438

(22) Filed: Oct. 11, 2021

(65) Prior Publication Data

US 2022/0204650 A1 Jun. 30, 2022

Related U.S. Application Data

(63) Continuation of application No. 14/505,722, filed on Oct. 3, 2014, now abandoned.

(60) Provisional application No. 61/889,743, filed on Oct. 11, 2013.

(51) Int. Cl.
*C07K 17/14* (2006.01)
*H01G 9/20* (2006.01)
*H10K 85/00* (2023.01)

(52) U.S. Cl.
CPC ........... *C07K 17/14* (2013.01); *H01G 9/2059* (2013.01); *H10K 85/761* (2023.02)

(58) Field of Classification Search
CPC .... C07K 17/14; H01G 9/2059; H10K 85/761; H10K 10/701; H10K 30/81
See application file for complete search history.

(56) References Cited

U.S. PATENT DOCUMENTS

| | | | |
|---|---|---|---|
| 2010/0327262 A1* | 12/2010 | Carmeli | B82Y 20/00 438/1 |
| 2012/0264144 A1* | 10/2012 | Jose | C12N 11/00 435/69.6 |
| 2013/0000723 A1 | 1/2013 | Willner et al. | |
| 2013/0011954 A1 | 1/2013 | Lebedev et al. | |
| 2013/0092237 A1 | 4/2013 | Takshi et al. | |

OTHER PUBLICATIONS

Den Hollander et al., Enhanced Photocurrent Generation by Photosynthetic Bacterial Reaction Centers through Molecular Relays, Light Harvesting Complexes, and Direct Protein Gold Interactions, Langmuir 2011, 27, 102892-10294.*
Supporting Information of Lebedev et al. (Supporting Information, Conductive wiring of immobilized photosynthetic Reaction Center to electrode by Cytochrome c, 2006, JACS, pp. 1-3) (Year: 2006).*
(Continued)

*Primary Examiner* — James Lin
*Assistant Examiner* — Sommer Yousef Osman
(74) *Attorney, Agent, or Firm* — Quarles & Brady LLP

(57) ABSTRACT

In some embodiments, a bioelectronic device includes an electrode, target proteins, and attachment mechanisms that immobilize the target proteins on the electrode, the attachment mechanisms comprising linker proteins that interface with the target proteins and attach the target proteins to the electrode.

9 Claims, 10 Drawing Sheets

(56) References Cited

OTHER PUBLICATIONS

University of Wisconsin-Madison, "Overview: Three-electrode setup", 2024, New electrochemistry SOP, pp. 1-19, https://berry.chem.wisc.edu/sites/berry.chem.wisc.edu/files/styles/medium/public/New%20electrochemistry%20SOP.pdf (Year: 2024).*

Díaz-González et al., Development of an immunosensor for the determination of rabbit IgG using streptavidin modified screen-printed carbon electrodes, 2005, Talanta, 65, pp. 565-573 (Year: 2005).*

Mahmoudzadeh et al., Photocurrent generation by direct electron transfer using photosynthetic reaction centres, 2011 Smart Materials and Structures, 094019, pp. 1-6 (Year: 2011).*

Ley et al., Immobilization of histidine-tagged proteins on electrodes, 2011, Colloids and Surfaces B: Biointerfaces, 88, pp. 539-551 (Year: 2011).*

Ibii et al., Direct Immobilization of Gold-Binding Antibody Fragments for Immunosensor Applications, 2010, Anal. Chem., 82, pp. 4229-4235 (Year: 2010).*

Avila, A. et al., An Electromechanical Approach to Investigate Gated Electron Transfer Using a Physiological Model System: Cytochrome c Immobilized on Carboxylic Acid-Terminated Alkanethiol Self-Assembled Monolayers on Gold Electrodes, Journal of Physical Chemistry B, 2000, 104(12):2759-2766.

Den Hollander, M. et al., Enhanced Photocurrent Generation by Photosynthetic Bacterial Reaction Centers through Molecular Relays, Light-Harvesting Complexes, and Direct Protein—Gold Interactions, Langmuir, 2011, 27:10282-10294.

Gerster, D. et al., Photocurrent of a Single Photosynthetic Protein, Nature Nanotechnology, 2012, 7:673-676.

International Energy Agency, Energy Technology Perspectives 2015, http://www.iea.org/etp/, 4 pages.

International Energy Agency, World Energy Outlook 2012, 690 pages.

Lebedev, N. et al., Conductive Wiring of Immobilized Photosynthetic Reaction Center to Electrode by Cytochrome c, J. Am. Chem. Soc., 2006, 128:12044-12045.

Lebedev, N. et al., Increasing Efficiency of Photoelectronic Conversion by Encapsulation of Photosynthetic Reaction Center Proteins in Arrayed Carbon Nanotube Electrode, Langmuir, 2008, 24:8871-8876.

Lewis, N. et al., Powering the Planet: Chemical Challenges in Solar Energy Utilization, PNAS, 2006, 103 (43):15729-15735.

Noll, T. et al., Strategies for "Wiring" Redox-Active Proteins to Electrodes and Applications in Biosensors, Biofuel Cells, and Nanotechnology, Chem. Soc. Rev., 2011, 40:3564-3576.

Reiss, B. et al., Evaluation of the Photosynthetic Reaction Center Protein for Potential Use as a Bioelectronic Circuit Element, Biotechnology Progress, 2007, 23(4):985-989.

Renewable Energy Policy Network for The 21st Century, Renewables 2011—Global Status Report, 116 pages.

Tan, S. et al., Increasing the Open-Circuit Voltage of Photoprotein-Based Photoelectrochemical Cells by Manipulation of the Vacuum Potential of the Electrolytes, ACS Nano, 2012, 6(10):9103-9109.

Trammell, S. et al., Effects of Distance and Driving Force on Photoinduced Electron Transfer between Photosynthetic Reaction Centers and Gold Electrodes, J. Phys. Chem. C, 2007, 111:17122-17130.

U.S. Energy Information Administration, Annual Energy Outlook 2013 with Projections to 2040, DOE/EIA-0383(2013), Apr. 2013, 244 pages.

Yaghoubi, H. et al., The Role of Gold-Adsorbed Photosynthetic Reaction Centers and Redox Mediators in the Charge Transfer and Photocurrent Generation in a Bio-Photoelectrochemical Cell, Journal of Physical Chemistry C, 2012, 116:24868-24877.

* cited by examiner

SYSTEMS AND METHODS FOR IMMOBILIZING A TARGET PROTEIN

CROSS-REFERENCE TO RELATED APPLICATION(S)

This application is a continuation of U.S. patent application Ser. No. 14/505,722, filed Oct. 3, 2014, which claims the benefit of priority of U.S. Provisional Patent Application No. 61/889,743, filed Oct. 11, 2013, each of which are hereby incorporated by reference herein in their entirety.

BACKGROUND

World energy consumption has deep implications for humanity. The world energy demand in 2010 was approximately 16 tetrawatts (TW). Population growth affects energy usage through increases in housing, commercial floor-space, transportation, and economic activity. The Annual Energy Outlook 2013 (AEO2013) estimated that the United States (U.S.) population will increase by 0.9% per year from 2011 to 2040, the economy, as measured by gross domestic product (GDP), will increase at an average annual rate of 2.5%, and the total energy consumption will increase by 0.3% per year. Furthermore, the total population of the world in 2050 is expected to be 10 billion. If these estimates are correct, the world energy demand in 2050 will be approximately 28 TW, which is nearly double what the demand was in 2010.

According to AEO2013, coal-fired power plants continue to be the largest source of electricity generation. The goal of limiting global warming to 2° C. is becoming more difficult and costly with each passing year. If action is not taken before 2017, all the allowable $CO_2$ emissions will be locked-in by the energy infrastructure that exists in 2017. Fossil fuels are dominant in the global energy mix, supported by $523 billion subsidies in 2011, up almost 30% from 2010 and six times more than subsidies to renewables.

Renewable energy comes from natural resources, including sunlight, wind, rain, tides, and geothermal heat, which are naturally replenished. As of 2010, about 16% of global final energy consumption came from renewables, with 10% coming from traditional biomass, which is mainly used for heating, and 3.4% coming from hydroelectricity. New renewables (e.g., small hydro, modern biomass, wind, solar, geothermal, and biofuels) accounted for another 2.8% and are rapidly growing. The share of renewables in electricity generation is around 19%, with 16% of global electricity coming from hydroelectricity and 3% coming from new renewables.

The advantages of renewable energy sources over fossil fuels have recently led to governmental investment on renewable energies, solar energy harvesting being the most important one. Harvesting solar energy with a cheap and sustainable technology could help speed up the transition from fossil fuels and into clean energy. The approach of covering vast swathes of desert in solar panels and piping the energy hundreds of miles through high-voltage transmission lines has not been successful to date. Instead, the key advantage of solar energy may be that it can cover houses, buildings, car parks, and other urban structures, enabling them to generate their own power. Unfortunately, current solar cell technologies are too expensive, especially for homeowners. The other often ignored topic in renewable energy strategies is the sustainability of the renewable energy technology itself.

The energy production cycle is being reshaped so it is clean, efficient, affordable, and the most sustainable alternative. Truly green technologies, wherein the active components for solar energy harvesting are photosynthetic proteins, have already been proposed. Photosynthesis evolved early in the evolutionary history of life and is a process used by plants and other autotrophic organisms to convert sunlight energy into chemical energy. In a photosynthetic organism, the primary energy conversion reactions take place in a reaction center protein (RC). The bacterial photosynthetic RC shows great promise for solar energy harvesting because of nearly 100% quantum yield of primary charge separation and an efficient stabilization of separated charges. In addition, active photosynthetic elements can be obtained at a low cost from either cultivated algae or agricultural remains, such as leaf stalks. Hence, the source is abundant, inexpensive, and truly sustainable.

Although the quantum efficiency in RCs is very high, efficient transfer of charges from RCs to electrodes of a photovoltaic device is challenging. Most fabricated RC-integrated protein-based cells to date have been comprised of a photoelectrochemical cell with RCs attached to a working electrode, immersed in an electrolyte with one or more redox mediators. In a photoprotein-based solar cell, the charge transfer rate between the RCs and the electrodes is a bottleneck for efficient biomolecule-based solar energy conversion. Previous applications of RCs in protein-based solar cells exhibited relatively low power conversion efficiency, mainly due to an inefficient electron transfer (ET) to or from an electrode. The ET process between the RCs and the electrodes is complicated by the fact that the RC's structure features a cavity at the charge site, which introduces a gap between the electrode and the protein.

From the above discussion, it can be appreciated that it would be desirable to increase the charge transfer rate between RCs and electrodes of an electrochemical bio-photovoltaic (bio-PV) device.

BRIEF DESCRIPTION OF THE DRAWINGS

The present disclosure may be better understood with reference to the following figures. Matching reference numerals designate corresponding parts throughout the figures, which are not necessarily drawn to scale.

FIG. 8(a) shows the normalized secondary edge measured with LIXPS before UPS; FIG. 8(b) shows the complete normalized UP spectra; and FIG. 8(c) shows the evolution of the valence bands (VB) emission features through the deposition process.

DETAILED DESCRIPTION

As described above, it would be desirable to increase the charge transfer rate between reaction center proteins (RCs) and electrodes of an electrochemical bio-photovoltaic (bio-PV) device. Disclosed herein are novel systems and methods for immobilizing target proteins, such as RCs, on an electrode, such as a working electrode of a bio-PV. In some embodiments, the target protein is immobilized using a linking protein that attaches the target protein to the electrode, either directly or indirectly. When such a linking protein is used to immobilize the target protein, greater electron transfer (ET) can be achieved.

In the following disclosure, various specific embodiments are described. It is to be understood that those embodiments are example implementations of the disclosed inventions and that alternative embodiments are possible. All such embodiments are intended to fall within the scope of this disclosure.

Disclosed are systems and methods for immobilizing target proteins on a conductive electrode for efficient charge transfer between the electrode and the protein. In one embodiment, systems and methods utilize the natural protein-protein interaction between two proteins to immobilize the target protein to the electrode. A linker protein can be attached to the electrode either directly (naturally adsorbed or functionalized proteins) or through another linker molecule (e.g., an oligomer molecule or a DNA). The immobilization occurs through the attachment of the target protein to the linker protein from a specific direction. This form of attachment facilitates charge transfer between the target protein and the electrode via the linker protein. This form of the immobilization can be used for various types of bio-electronic devices, including bio-PV devices as well as bio-sensors.

Figure 1:
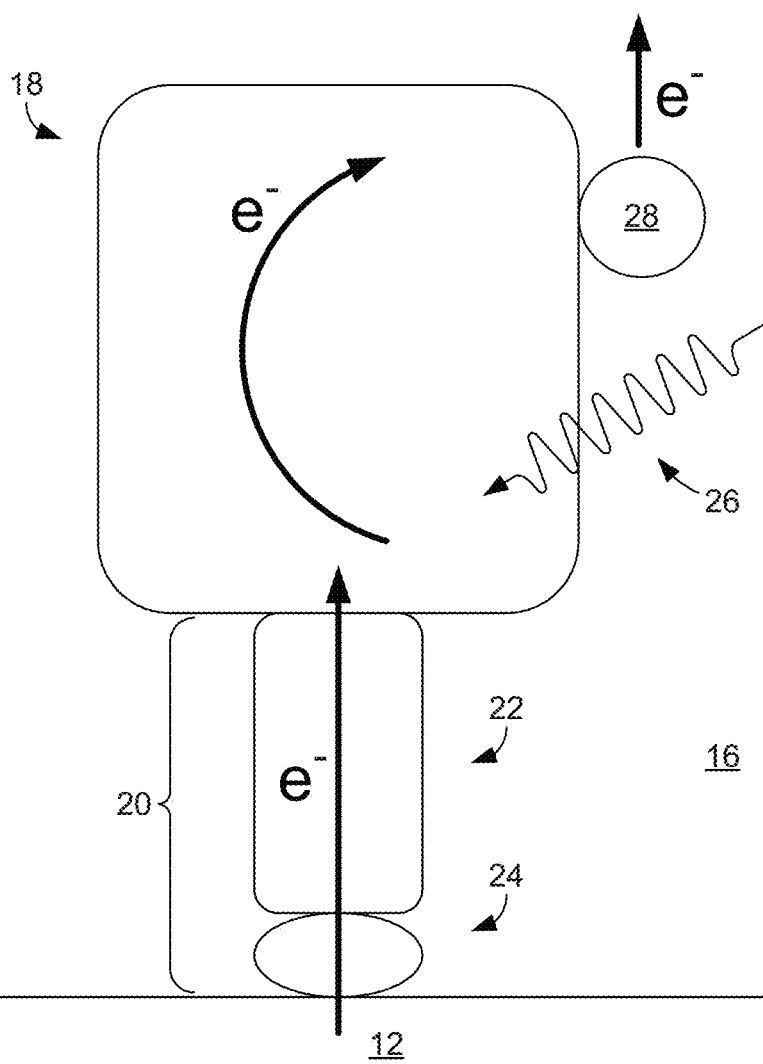
FIG. 1 is a schematic drawing illustrating an embodiment of a bio-electronic device having target proteins immobilized on a working electrode of the device.

FIG. 1 illustrates an example embodiment of a bio-electronic device 10 that incorporates the immobilization scheme described above. As shown in the figure, the device 10 includes a first or working electrode 12 that collects holes and a second or counter electrode 14 that collects electrons. The electrodes 12, 14 can be made of a suitable electrically conductive or semiconductive material. In some embodiments, the electrodes 12, 14 are made of a metal, such as gold (Au). The electrodes 12, 14 are separated by an electrolyte solution 16, which can comprise an aqueous solution of a gel media with charge carrier mediators, such as quinone or ferrocene.

Disposed in the electrolyte solution 16 between the electrodes 12, 14 are target proteins, including the target protein 18 identified in FIG. 1. The target protein 18 can comprise any protein that is to be immobilized on the working electrode 12. In some embodiments, the target protein 18 comprises an R. sphaeroides bacterium RC, R. sphaeroides bacterium RC-light harvesting complex (LH1) +Pufx (Pufx is an opening in the LH1 ring), R. sphaeroides bacterium RC-LH1 −Pufx (Pufx deficient), plant Photosystem I or II (PS-I or PS-II) protein, a protein complex from the phycobilisome protein family (phycocyanins have shown promise in harvesting sunlight energy), or a bacteriorhodopsin protein. R. sphaeroides bacterium RC, RC-LH1 +Pufx, and RC-LH1 −Pufx can be obtained from purple bacteria. A global source of photosynthetic RC is algae, while Photosystem I and II proteins can be obtained from spinach.

As is further illustrated in FIG. 1, the target protein 18 is attached to, and therefore immobilized on, the working electrode 12 with an attachment mechanism 20, which may be referred to as a molecular wire or a hybrid wire. The attachment mechanism 20 at least includes a linker protein 22 that is directly attached to the target protein 18. In particular, the target protein 18 attaches to the linker protein 22 because of the natural interaction between proteins, which can be referred to as a docking effect. The linker protein 22 can comprise any protein to which the target protein 18 can attach. The linker protein 22 that is used depends at least in part upon the target protein 18 that is to be immobilized. In embodiments in which the target protein 18 is RC, RC-LH1 +Pufx, or RC-LH1 −Pufx, the linker protein 22 can comprise cytochrome c. Any of Classes I-IV cytochrome c can be used. Class I includes the lowspin soluble cytochrome c of mitochondria and bacteria. It has the heme-attachment site towards the N terminus of histidine and the sixth ligand provided by a methionine residue towards the C terminus. Class II includes the highspin cytochrome c. It has the heme-attachment site closed to the N terminus of histidine. Class III comprises the low redox potential multiple heme cytochromes. The heme c groups are structurally and functionally nonequivalent and present different redox potentials in the range 0 to −400 mV. Class IV was originally created to hold the complex proteins that have other prosthetic groups as well as heme c.

The mechanism of attachment between cytochrome c and target proteins is based on protein-protein docking via short-range non-polar and long-range electrostatic forces. This mechanism likely brings the cytochrome c heme and the RC P cofactors into proximity for efficient ET. Cytochrome c heme is a heme iron (heme iron is one of two forms of iron occurring in foods). Therefore, different types of high-potential iron-sulfur proteins (known as HiPIPs) can be used as the electron-mediating layer (linker protein).

When the target protein 18 is one from Photosystem I or II, the linker protein 22 can comprise an electron mediating layer, such plastocyanin or cytochrome c. When the target protein 18 is one from the phycobilisome protein family, the linker protein 22 can comprise a native or an engineered linker based on phycobilisome.

In the embodiment illustrated in FIG. 1, the attachment mechanism 20 further includes a linker molecule 24 that is positioned between the linker protein 22 and the working electrode 12. The linker molecule 24 provides a stable bond, with a preferential orientation of attachment between the linker protein 22 and the working electrode 12. The linker molecule 24 also might prevent the linker protein 22 from undergoing conformational changes. However, if the linker molecule 24 is not needed, the structure can be fabricated by direct attachment of a linker protein 22 to the working electrode 12. The linker molecule 24 can be electrically conductive, semiconductive, or insulative. Example linker molecules 24 include insulator linker molecules, conjugated molecules, conducting polymers, deoxyribonucleic acid (DNA), nanoparticles, and mixtures thereof.

In some embodiments, the linker molecule comprises a carboxylic acid terminated alkanethiol linker, which is an insulative linker molecule. Although use of such a linker molecule is viable, it can lead to losses in electron transfer from the working electrode 12 to the linker protein 22. These losses can be mitigated to eliminate the energy barrier between the electrode 12 and the linker protein, which act as an electron transfer mediating layer. Judicious selection of conductive linker molecules with an energy level between the electrode work function and the energy level in the linker protein 22 will reduce the energy barrier and enhance ET.

A variety of linker molecules with conjugated structures that have the mentioned energy structure (and make the electrode surface wetting characteristics, hydrophilic) can be used as conductive linkers. P-type conjugated small molecules and polymers that exhibit strong absorption of sunlight spectra can be used due to the ease of film formation, good charge mobility, and suitable frontier orbital energy levels. In some embodiments, the linker molecule 24 can be an oligomer of thiophene and ethylenedioxythiophene, regioregular poly (3-hexylthiophene) (rr-P3HT), or pPoly (3, 4-ethylenedioxythiophene) (PEDOT). The HOMO level in regioregular poly (3-hexylthiophene) (rr-P3HT) is close to the energy level at the primary electron donor side of the photosynthetic protein. The energy level of pPoly (3, 4-ethylenedioxythiophene) (PEDOT) enables it to function as linker molecule. Both rr-P3HT and PEDOT are popular conducting polymers. In theory, a higher efficiency can be achieved by using a combination of RCs and conducting polymers.

When the target proteins have been immobilized on the working electrode in the manner described above, the bio-electronic device 10 can be operated. FIG. 1 illustrates an example of operation of the device. In this figure, photons 26 incident upon the target protein 18 are absorbed by the protein and unbound electron-holes are generated. The electrons are transferred as indicated by the arrows. Charges from the target protein 18 can be transported from the target protein to the counter electrode 14 via charge carriers, such as charge carrier 28 shown in FIG. 1. In some embodiments, the charge carrier 28 comprises one or more of a soluble redox mediator such as quinone, ferrocene (Cp2Fe), ferrocyanide, methyl viologen (MV), N,N,N',N'-tetramethyl-p-phenylenediamine (TMPD), and phenazine methosulfate (PMS).

Figure 2:
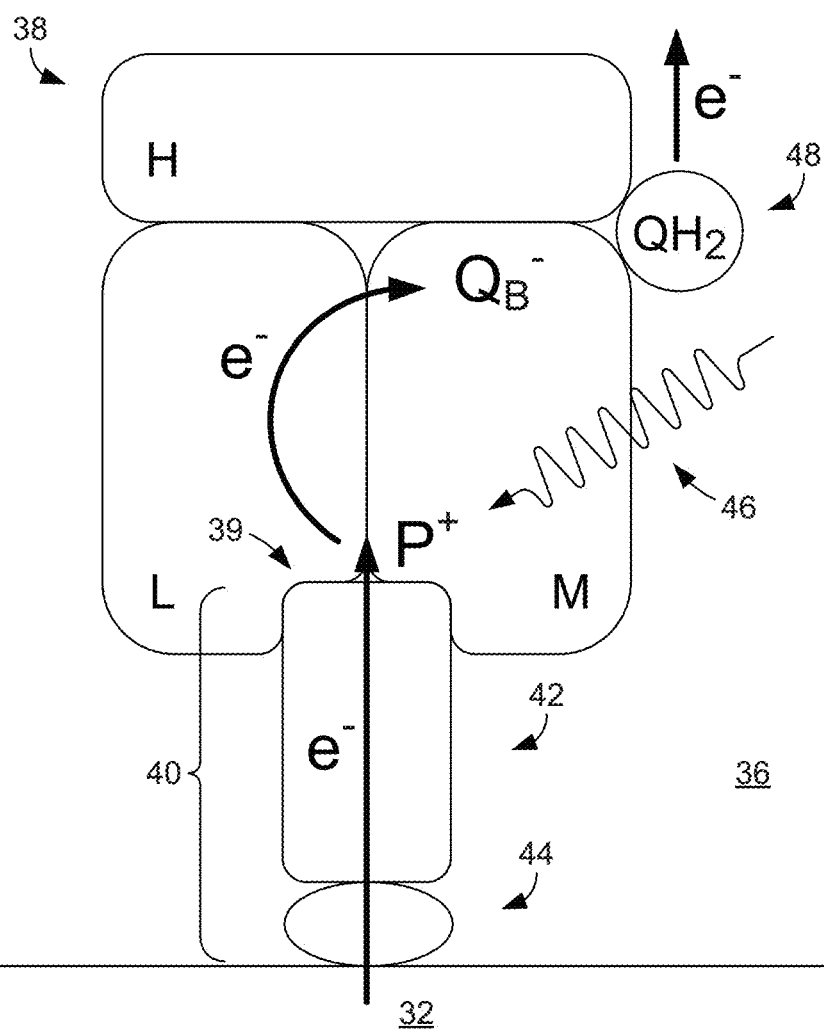
FIG. 2 is a schematic drawing illustrating an embodiment of an electrochemical bio-photovoltaic device having photosynthetic reaction center proteins (RCs) immobilized on a working electrode of the device.

FIG. 2 illustrates a further example embodiment of a bio-electronic device 30. In this embodiment, the device 30 is configured as an electrochemical bio-PV device. The device 30 is similar in many ways to the device 10 shown in FIG. 1. Accordingly, the device 30 comprises a first or working electrode 32, a second or counter electrode 34, and an electrolyte solution 36, each of which can have a configuration similar to that described above for like-named components. The device 30 includes a photosynthetic reaction center protein (RC) 38, which is a protein complex that comprises three protein subunits L, M, and H that form a cavity or bowl 39. As is depicted in FIG. 2, the cavity 39 is docked on an attachment mechanism 40 that comprises equine heart cytochrome c 42 as the linker protein and a linker molecule 44, such that the RC 38 is immobilized on the working electrode 32.

When the RC 38 is exposed to sunlight, a photocurrent is generated by transferring one of the charges (positive or negative) from the RC to the working electrode 32. The curved arrow inside the RC 38 shows the path of electron transfer from the primary donor ($P^+$) to the final acceptor ($QB^-$) upon absorbing a photon 46. Opposite charges are moved to the counter electrode 34 by a charge carrier 48.

Figure 3:
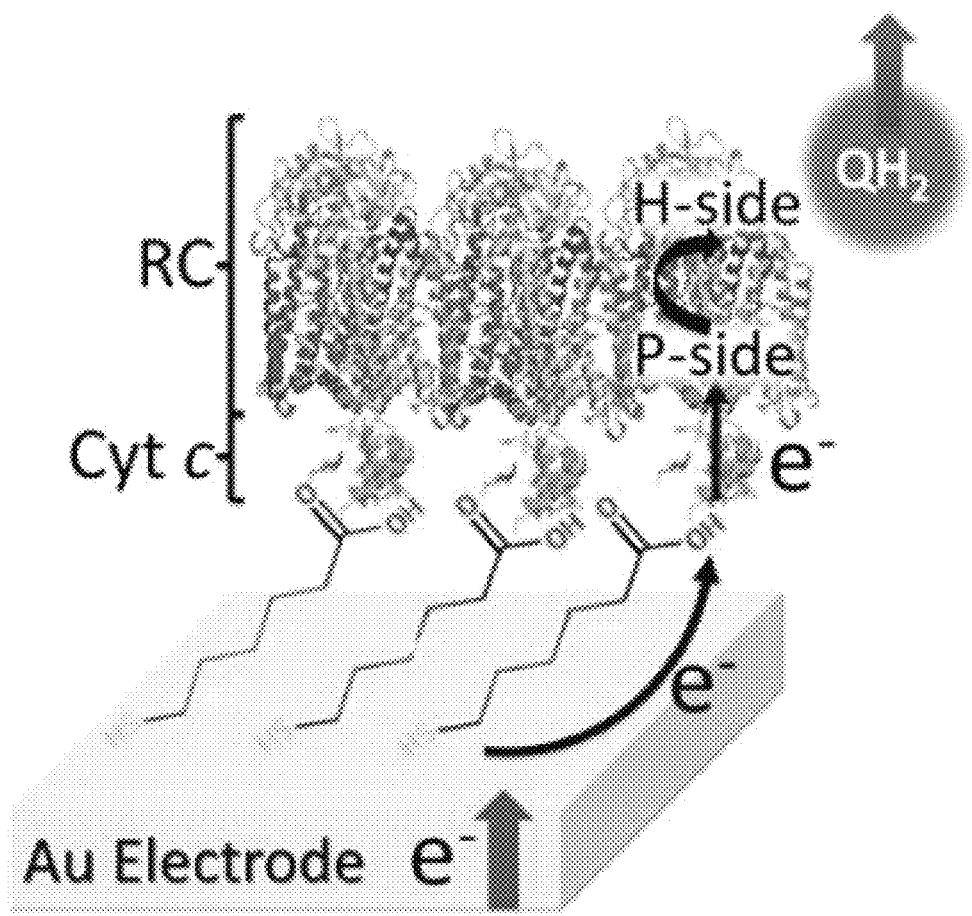
FIG. 3 is a schematic drawing illustrating the structure of a working electrode of an electrochemical bio-photovoltaic device having RCs immobilized on a gold working electrode using a carboxylic acid-terminated alkanethiol self-assembled monolayer (SAM) and a layer of cytochrome c.

A further representation of the immobilization of RCs with cytochome c and linker molecules is provided in FIG. 3.

A hybrid oligomer-protein molecular wire was studied for immobilizing the wild-type RC from the P-side onto a Au electrode and at the same time filling the bowl of the RC to obtain a higher peak photocurrent density as compared to that in the previous work. This structure was assembled through a layer-by-layer deposition of a self-assembling monolayer (SAM) with carboxylic acid terminal groups (the linker molecules), cytochrome c (cyt c) (the linker proteins), and RC proteins (the target proteins). Because the feasibility of immobilizing cyt c onto a Au electrode using 6-mercaptohexanoic acid has been demonstrated before, the same molecule was utilized to construct the hybrid SAM|cyt c linker for RCs. The goal was to obtain RC immobilization, which occurs via the docking interaction between RC and cyt c. It was assumed that this mechanism could bring the cyt c heme and the RC P cofactors into proximity for efficient ET. The results described below show that the structure binds the RC without any need for protein mutation. Additionally, the observed photocurrent density evidenced successful docking between cyt c and RC.

All materials, including equine heart cyt c, were purchased from Sigma-Aldrich except for the RC protein. Wild-type RC from Rhodobacter sphaeroides was prepared using LDAO for solubilization. Cells were centrifuged at 9,000 g and re-suspended in 10 mM Tris (pH 8), 150 mM NaCl, and 2 mM $MgCl_2$. A few crystals of DNase A were added to the suspension, and the cells were broken by two passages through a French press. Broken cells were centrifuged at 9,000 g to pellet unbroken cells and the supernatant centrifuged overnight at 30,000 rpm in a Beckman Coulter Type 70 Ti rotor to pellet membranes. Membranes were re-suspended in 10 mM Tris (pH 8) and 150 mM NaCl and solubilized with 1.5% N,N-dimethyldodecylamine N-oxide (LDAO). Solubilized membranes were ultracentrifuged at 541,000 g, and six His-tagged RCs were purified from the supernatant using affinity chromatography. Planar Au working electrodes were fabricated by evaporating an adhesive Cr layer (20 nm) followed by deposition of 400 nm thick Au layers onto the cleaned glass substrates. The Au electrodes were cleaned by rinsing sequentially with acetone, methanol, isopropanol, and deionized water and dried completely under a $N_2$ stream prior to performing experiments. The Au|SAM|cyt c|RC electrode was fabricated by treating a cleaned Au electrode in a 10 mM 6-mercaptohexanoic acid (lower concentrations of linker molecules resulted in lower photocurrents) over five days at room temperature, rinsing the electrode in 0.1 M Tris-HCL (pH 8) buffer, followed by immersing in a 0.8 mM cyt c solution for a day at 4° C., rinsing with buffer, and immersing in a 1.0 µM solution of RCs at 4° C. for a day. Weakly bound RCs were removed from the electrode by rinsing the electrode with buffer.

The fabricated electrode was used in an electrochemical cell as the working electrode. A 13 cm length of Pt wire of 0.25 mm diameter was shaped into a coil and used as the counter electrode. A 60 µM solution of coenzyme Q2 (2, 3-dimethoxy-5-methyl-6-geranyl-1, 4-benzoquinone, hereafter referred to as Q) in 0.1 M Tris buffer was used as the electrolyte. It was shown that the above-mentioned concentration does not limit the current in a cell with the RC proteins. For the experiments in which a reference electrode was needed, an Ag/AgCl electrode was used. All the experiments were performed at room temperature using 0.1 M Tris-HCl at pH 8 as the background electrolyte. The current polarity convention was set in a fashion that defined cathodic current as negative. Each cell was kept in the dark until the open-circuit potential (OCP) stabilized. For the photocurrent measurements, the same potential was applied to the cell by the potentiostat such that the current in the dark was zero. The cells were illuminated with a commercial solar simulator (RST300S (AM 1.0)), Radiant Source Technology) at an incident light intensity of 80 mW $cm^{-2}$ at the electrode's surface. The solar light source uses a XL3000 PerkinElmer Fiber Optic Illumination (FOI) system that employs a 300-watt Cermax Xenon light. Photocurrents and photovoltages were recorded using a VersaSTAT 4 (Princeton Applied Research) potentiostat in both three and two electrode setups. The three electrode measurements were performed to accurately study the reactions only on the surface of the working electrode (the potential changes of the working electrode are measured independent of changes that may occur at the counter electrode). Hence, the surface area of Pt counter electrode would not be a rate limiting factor.

Light from a tungsten halogen lamp (Oriel 6334NS 24 V, 250 W) was focused onto the entrance slit of a monochromator (Cornerstone 260¼M) using a pair of parabolic mirrors. The dispersed light passing through the exit slit (slit width: 5 nm) was subsequently focused onto the device using a convex lens. The photocurrent was measured from 590 nm to 950 nm in steps of 6 nm in the three-electrode cell. At each wavelength step, the photocurrent was monitored for two complete cycles consisting of 20 seconds of illumination followed by 20 seconds in the dark, during which the light was blocked by a computer controlled shutter at the exit slit of the monochromator. The incident power was measured by a thermopile detector (Oriel 71945) connected to a multimeter (Keithley2000). The EQE was measured as the ratio of collected electrons to incident photons. The equation for calculation is thus:

$$EQE = 100 \times \frac{J \cdot \hbar\omega}{e \cdot I} \qquad \text{Eq. (1)}$$

where J is the current density in A $cm^{-2}$, e is the electron charge in C, I is the incident photon power density in Watts $cm^{-2}$, and $\hbar\omega$ is the energy per photon in Joules, all at the wavelength λ.

The thickness measurements were performed using a Rudolf Research Type ellipsometer AutoEL (wavelength of 6328 Å (He—Ne laser)) at an incident angle of 70° for carboxylic acid-terminated SAMs; a Sopra spectroscopic ellipsometer ES 4G (multilayer optical spectrometric scanner) at an incident angle of 70.1° was used for the cyt c and RC layers. The refractive index and the coefficient of absorption values for the Au substrates were measured to be 0.1508 and 3.3280, respectively. The ellipsometric data were analyzed assuming an index of refraction of 1.4846 for the SAM monolayer, as suggested by the supplier (Sigma-Aldrich).

For photoemission spectroscopy, all samples were prepared in a glovebox that was outfitted to the fast load lock of a multi-functional characterization system. This commercial multi-chamber system (SPECS, Berlin, Germany) consists of two preparation chambers and one analysis chamber outfitted for X-ray photoemission spectroscopy (XPS). The base vacuum level of this system is $2 \times 10^{-10}$ mbar. An Mg Kα X-ray emission source with incident energy of 1253.6 eV and 20 mA emission current was used for the core level XPS. Low intensity XPS (LIXPS) measurements were performed prior to the XPS in a standby mode with 0.1 mA emission current. The corresponding significantly low amount of photon flux was generated and used to measure the sample work function (WF) free of charging artifacts. The ultraviolet photoemission spectroscopy (UPS) measurement was carried out with a SPECS UVS10/35 UV source by discharging highly pure helium gas (99.99%). The He I line was generated by controlling the discharging voltage in a range of 600 V to 750 V. The data analysis was performed using Igor Pro software. The energy gap of the linker molecule was estimated from the optical absorption spectrum using a Thermo Scientific (Evolution 201) UV-Vis spectrophotometer.

Figure 4A:
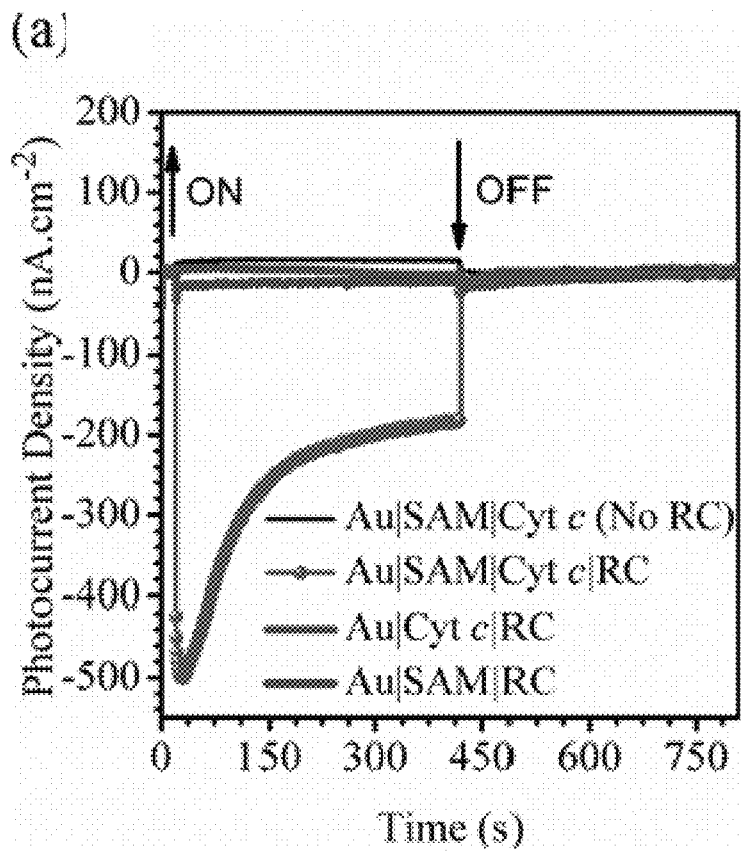
FIG. 4(a) is a graph that shows the time dependence photo-response of a fabricated bio-photoelectrochemical cell under 80 mW $cm^{-2}$ illumination with coenzyme Q as the single diffusible redox mediator. In the graph, the up arrows indicate light "on" and the down arrows indicate light "off" with the current obtained from the configurations shown as nA $cm^{-2}$ according to the key.

The photocurrent density of the Au|SAM|cyt c|RC structure was measured in both three and two electrode setups. As shown in FIG. 4(a), in a three electrode experiment, a cathodic photocurrent was achieved after the electrode was illuminated. By immobilizing RCs using the hybrid SAM-|cyt c linker, a peak current density of up to 0.5 µA $cm^{-2}$ was achieved, which is at least three times of that using random diffusion of cyt c proteins in previous work. The photocurrent density stabilized at −185 nA $cm^{-2}$ after 400 s while the working electrode was held at the dark open circuit potential (OCP) of +0.05 V versus a normal hydrogen electrode (NHE). There was an initial spike of photocurrent at the onset of illumination similar to what has been observed in a recent work. It was reasoned that this initial spike was originated from a kinetic limitation at the RC's primary acceptor side (QB−) due to the different rates of P+ reduction and QB− oxidation, which results in buildup of negative charges within the protein. Accordingly, the overoxidation of the redox mediator equilibrates the charge accumulation inside the RC.

To confirm the contribution of the protein complexes to the photocurrent generation, control experiments were performed on a cell containing an Au|SAM|cyt c working electrode and Q as the charge carrier, but without any RC protein component. The negligible photocurrent density in the Au|SAM|cyt c structure (see FIG. 4(a)) demonstrates that the photocurrent stems from the charge generation in the RC. The cathodic photocurrent in the Au|SAM|cyt c|RC structure implies ET from the Au electrode to the RC, which suggests the protein orientation with the primary donor (P-side) facing the electrode. Hence, the majority of cyt c molecules were likely bound to the P-side of the RC protein complex. Adding more cyt c to the electrolyte did not enhance the photocurrent, which supports the interpretation that the majority of the RCs were docked onto SAM-bound cyt c proteins. The photochronoamperometric study of the two electrode setup resulted in a short circuit steady-state photocurrent density (JSC) of −156 nA cm$^{-2}$ and a steady-state open circuit voltage (VOC) of ~90 mV under continuous illumination. As described below, the energy barrier at the SAM is one of the limiting factors for an efficient charge transfer and energy conversion. However, the very low photocurrent from an electrode without any SAM (Au|cyt c|RC in FIG. 4(a)) shows the importance of the linker molecule in a successful use of the incubated cyt c for the RC immobilization. In addition to the poor binding of cyt c to the electrode in the absence of the SAM, the low photocurrent may be due to variable orientation of cyt c upon adsorption on Au and/or cyt c conformational changes, protein unfolding, and even denaturation on this bare metal electrode.

Figure 4B:
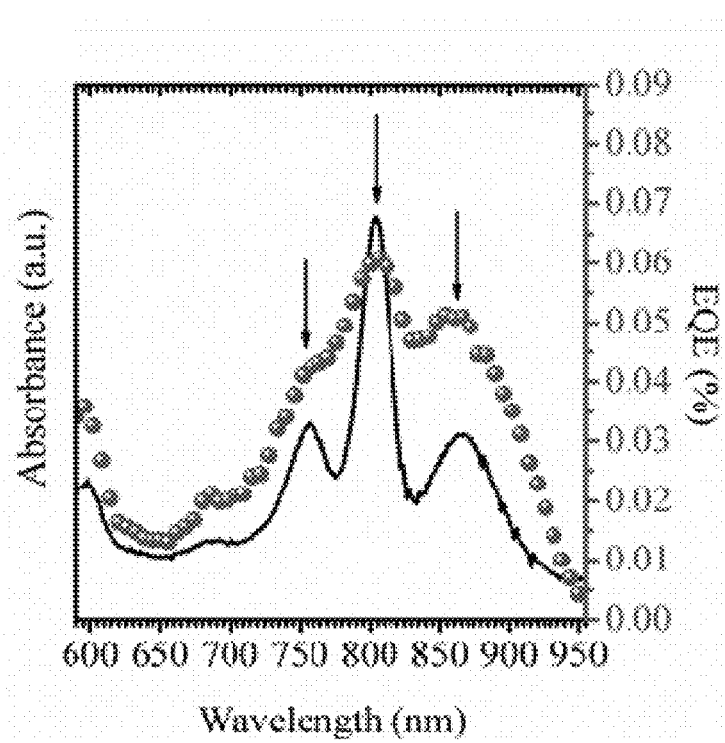
FIG. 4(b) is a graph that shows the external quantum efficiency (EQE) of the photocurrent, per incident photon, generated on a Au|SAM|cyt c|RC electrode (dots) compared to the absorption spectrum of the RC (solid line).

To further verify that the observed photocurrent in the Au|SAM|cyt c|RC cell stems from the photon absorption and charge generation by RCs, a photocurrent action spectrum was obtained across 590 nm to 950 nm and the EQE (%) was estimated, as well. FIG. 4(b) shows a substantial match between the RC absorption spectrum and the efficiency of photocurrent generation across this wavelength range. The distinctive triplets of RC cofactor absorptions are clearly present in the EQE spectrum.

Figure 5:
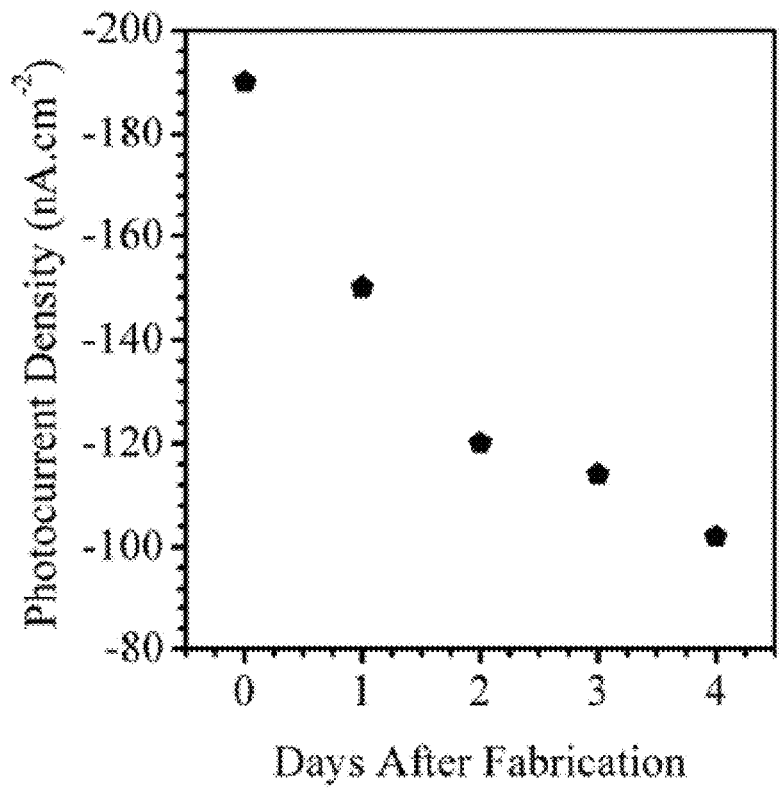
FIG. 5 is a graph that shows the change in the steady-state photocurrent density of a cell measured over a course of five days (one test each day).

The stability of the Au|SAM|cyt c|RC structure was studied further by measuring the photocurrent density of a single electrode over a course of five days. As shown in FIG. 5, the magnitude of the photocurrent density dropped from 185 nA cm$^{-2}$ for a fresh electrode to 102 nA cm$^{-2}$ after four days of storage in aerobic condition. These results show that despite the lack of a covalent bond between RC and cyt c, the protein-protein interaction is strong enough to hold more than half of the RCs after four days in aerobic conditions, while the protein complexes kept their integrity and functionality. The result suggests that the rate of reduction in the photocurrent density is faster in the first couple of days. This could be due to the degradation of fraction RC complexes. Extended device lifetime by appropriate sealing and oxygen removal can be achieved. Additionally, these results show that despite the lack of a covalent bond between RC and cyt c, the protein-protein interaction is strong enough to hold more than half of the RCs after four days, in aerobic conditions, while the protein complexes kept their integrity and functionality.

Figure 6:
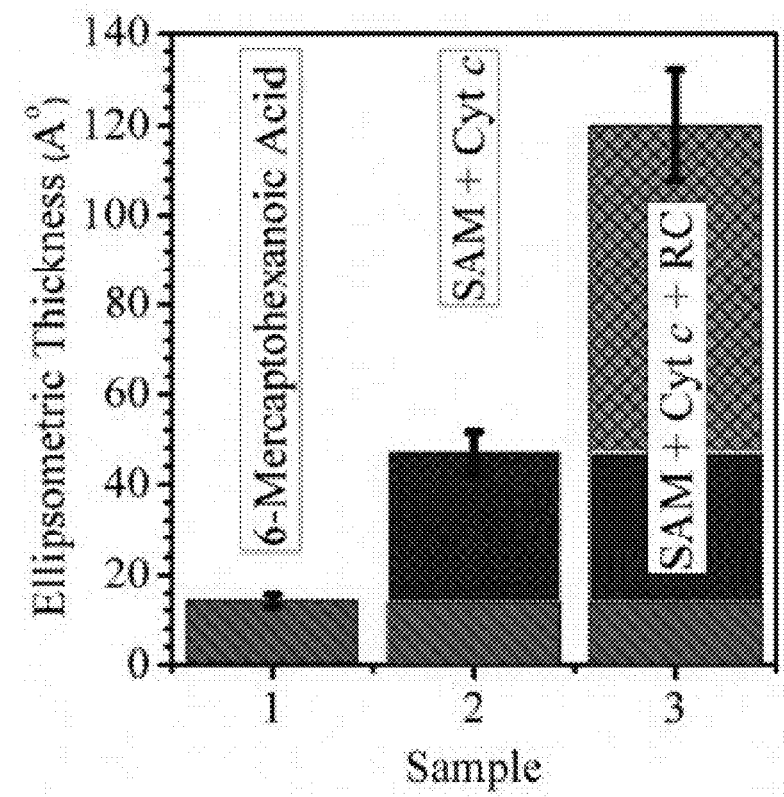
FIG. 6 is a graph that shows the ellipsometric estimation of the thickness of three samples: Sample 1: SAM of 6-mercaptohexanoic acid; Sample 2: SAM|cyt c; and Sample 3: SAM|cyt c|RC.

The Au|SAM|cyt c|RC structure was further studied by measuring the thickness of the SAM, SAM|cyt c, and SAM|cyt c|RC layers using ellipsometry. Ellipsometry can accurately measure the thickness and complex dielectric function of a given material. As shown in FIG. 6, the SAM prepared from 10 mM 6-mercaptohexanoic acid showed an approximately 14 Å thick layer. Assuming a 30° tilt for the alkanethiol chain, the measured thickness is slightly greater than the theoretical thickness expected for a close-packed monolayer oriented to the surface. This has been explained by coverage of a high free energy surface (i.e., Au) with reversibly physisorbed layers of water, hydrocarbons, and other organic compounds under laboratory ambient conditions. As shown in FIG. 6, the thickness of the SAM increased by approximately 33 Å after cyt c immobilization on top, which is in a good agreement with the size of cyt c reported by other groups. Upon deposition of the RCs, the thickness increased from approximately 47 Å to approximately 120 Å, indicating that a monolayer of RCs (thickness ~70 Å) had attached on top of the Au|SAM|cyt c.

Figure 7:
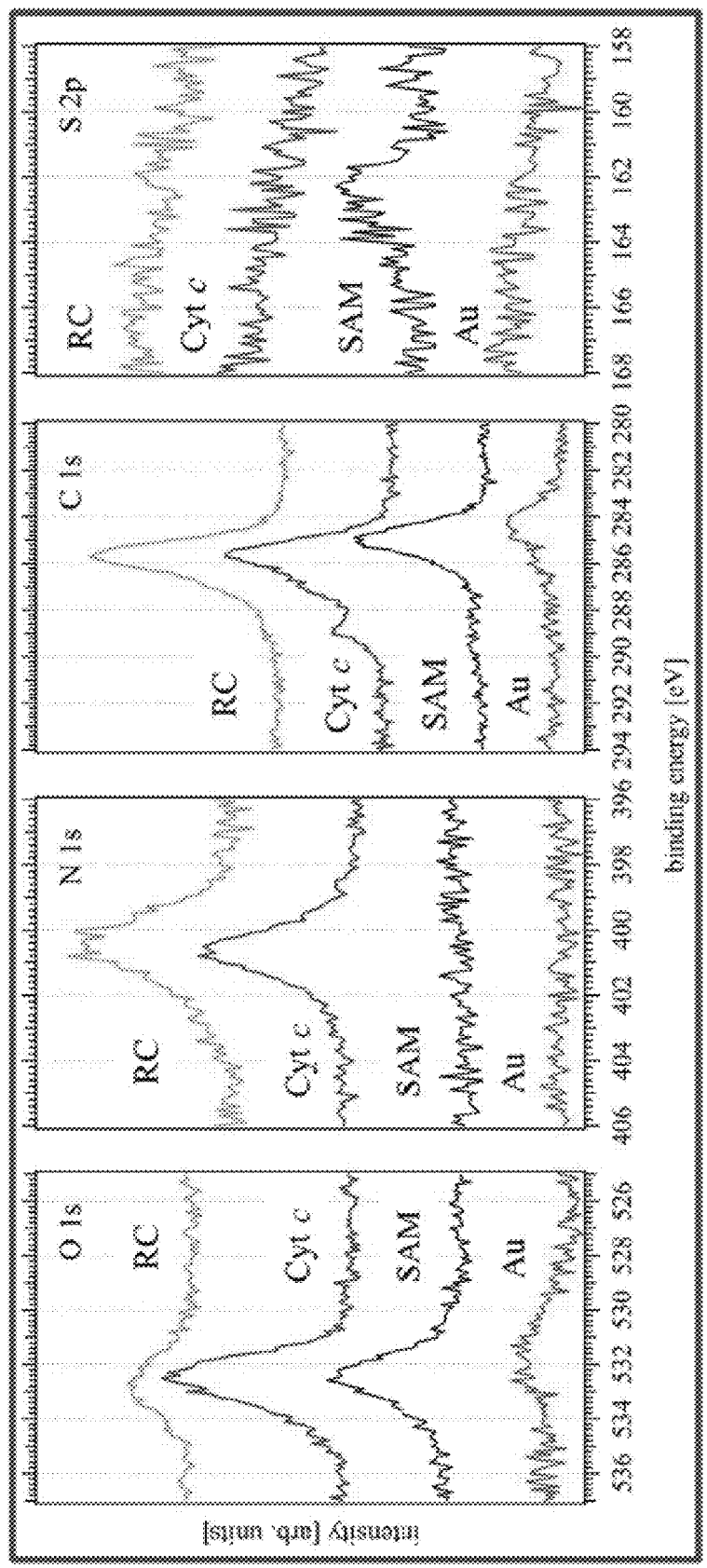
FIG. 7 is a graph that shows the x-ray photoemission spectroscopy (XPS) spectra of O1s, N1s, C1s, and S2p core level emissions for Au, Au|SAM, Au|SAM|cyt c, and Au|SAM|cyt c|RC samples.

To analyze the elemental composition on the electrode's surface, XPS was applied as a surface-sensitive quantitative spectroscopic technique. Also, XPS data provided further evidence for the successful attachment of the desired molecules. FIG. 7 shows XPS spectra of the O1s, N1s, C1s, and S2p core level lines acquired after each deposition step. The bottom spectra were obtained from the bare Au electrode which was free of nitrogen and sulfur, indicated by the absence of a peak in the N1s and S2p lines. Small peaks of O1s and C1s were observed, which are attributed to residual contamination on the Au surface remaining after the chemical cleaning process performed prior to the self-assembly of the alkanethiol layer. The successful self-assembly of alkanethiol molecules on the surface of Au electrodes was confirmed by the emergence of a weak peak in the S2p line, as well as the evolution of well-defined peaks in the O1s and C1s lines. The O1s line in black around 532.3 eV is attributed to C—OH and C═O species in the carboxyl group. The C1s spectrum exhibits a peak around 285.0 eV, which arises from the emissions of carbon species in the alkane group. The thiol group as the attachment anchor presents an S2p doublet line around 162.0 eV. Following the deposition of cyt c on top of the SAM, the O1s and C1s lines evolved accordingly. The O1s peak in blue has a similar shape and binding energy as from the SAM, but of greater amplitude. The O1s line is likely attributed to oxygen atoms in the backbone and side chains of cyt c. The C1s emission from cyt c shows a different shape and binding energy than that of the SAM alone. The peak around 285.4 eV is thought to arise from the aliphatic side chains of cyt c, whereas the weaker peak around 289.0 eV is attributed to the carbon atoms in the protein backbone. The emerging N1s peak in blue (cyt c) likely resulted from the N atoms of the peptide bond and N containing side chains and validates the adsorption of cyt c on the linker layer, which caused the attenuation of S2p photoelectrons from the SAM as shown by the loss of the peak in the S2p line.

The corresponding core level lines obtained after the addition of the RC layer on top of the cyt c film are shown in FIG. 7. The photoemission photons from cyt c were attenuated by the RC layer as indicated by the decreased intensity of the O1s peak and the loss of the minor peak in the C1s spectrum around 289.0 eV. The nitrogen species in the RC differ from those in the cyt c. These spectral changes confirm the attachment of the RC to the Au|SAM|cyt c, as opposed to binding of the RC nonspecifically, in which case the cyt c signal would not be expected to be attenuated.

Figure 8:
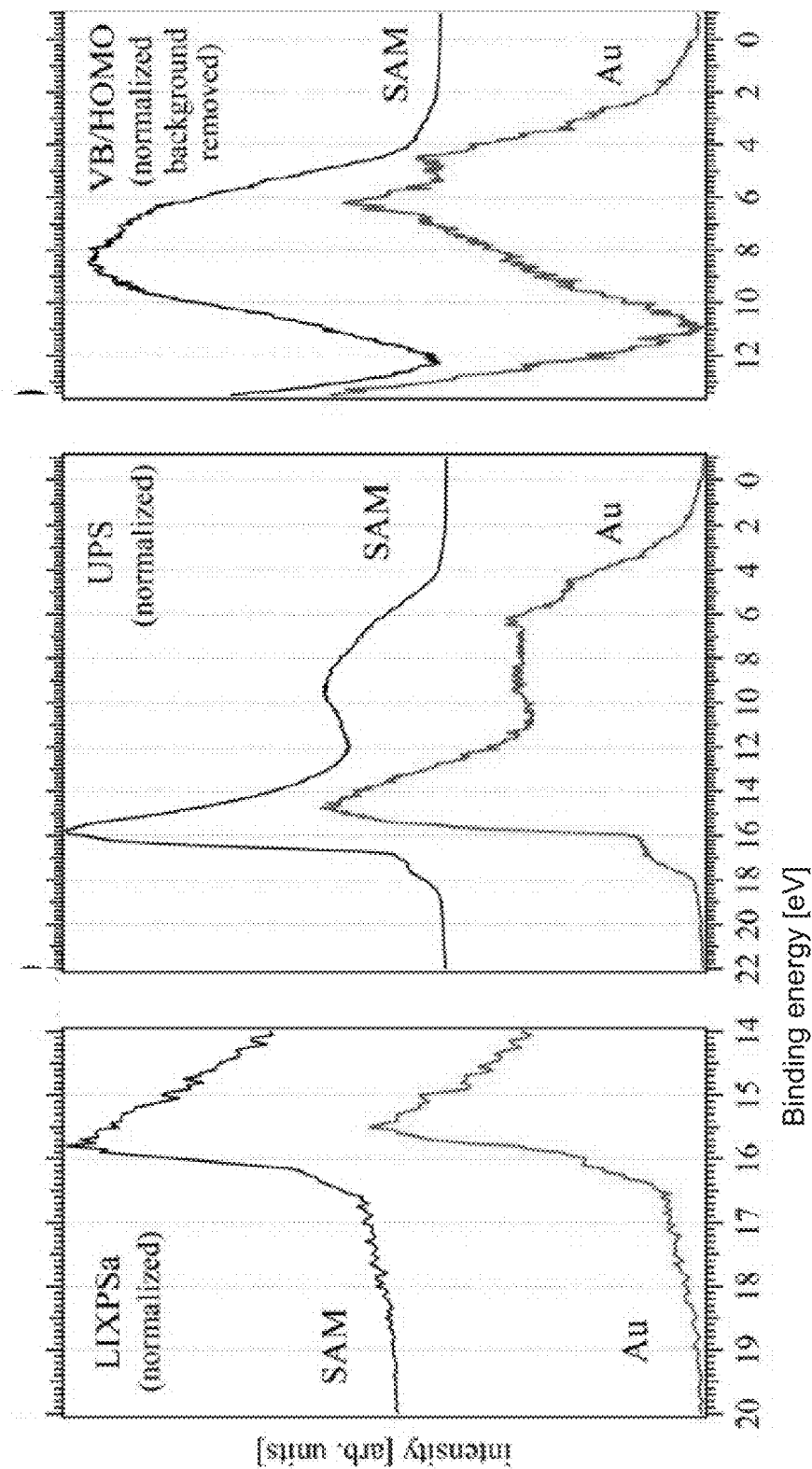
FIG. 8 includes graphs that show the low intensity XPS (LIXPS) and ultraviolet photoemission (UP) spectra before (bottom) and after (top) the deposition of a SAM on a clean Au substrate.

In order to evaluate how the energy levels of the SAM affect the ET between the Au electrode and RC, the highest-occupied-molecular-orbital (HOMO) and the lowest-unoccupied-molecular-orbital (LUMO) of the SAM were measured using LIXPS, UPS, and UV-Vis absorption spectroscopy methods. FIG. 8 shows the UPS spectra measured before and after deposition of the SAM during this experiment. The center panel (FIG. 8(b)) shows the complete spectra, and the side panels show the secondary edge normalized (FIG. 8(a)) as well as the valence bands region after background subtraction (FIG. 8(c)).

The secondary edge spectral cutoffs acquired via LIXPS (FIG. 8(a)) allowed for the determination of the WF of the Au and the Au|SAM substrates. The WF was calculated by subtracting the cutoff binding energy value from the excitation energy (21.2182 eV) and taking the analyzer broadening of 0.1 eV into account. FIG. 8(b) shows the complete set of normalized UPS. The main emission features include the Fermi level, the valence bands/HOMO (VB/HOMO) density of states, and the secondary edge. The magnified VB/HOMO spectra with background removed are shown in FIG. 8(c). Before deposition of a SAM, the valence bands and the Fermi level of the Au substrate can be clearly observed. After the deposition of a SAM, these features are suppressed and replaced by features corresponding to the emissions from the SAM. The valence bands maximum (VBM) of the Au electrode coated with a SAM relative to Au alone are shown in the magnified VB/HOMO spectra.

Figure 9:
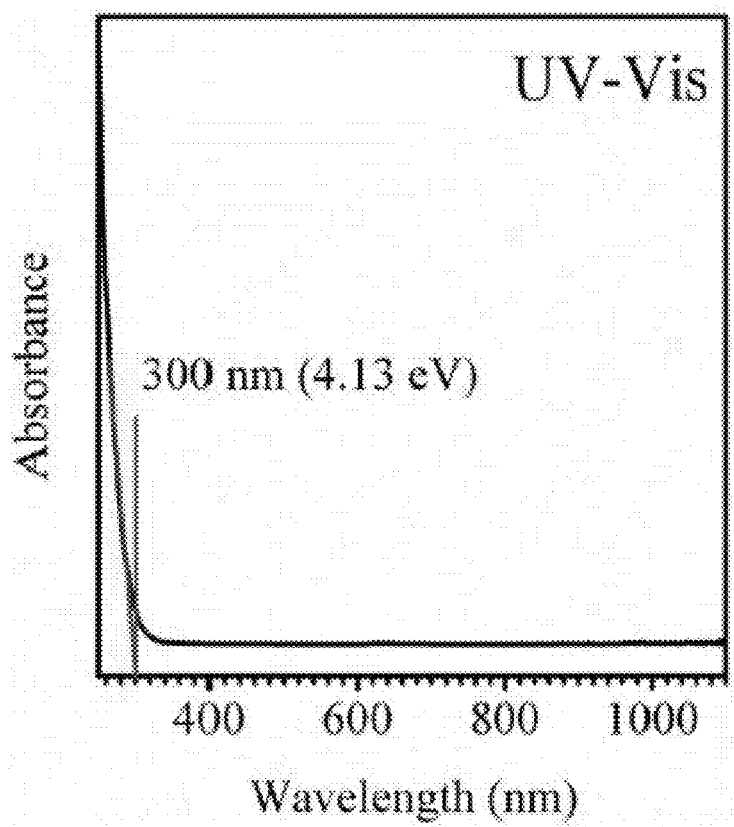
FIG. 9 is a graph that shows the UV-Vis absorption spectrum of the linker solution (10 mM 6-mercaptohexanoic acid).

In order to estimate the optical band/HOMO-LUMO gap in the linker molecule, the absorption spectrum of the linker solution (10 mM in ethanol) was measured. As shown in FIG. 9, the absorption threshold starts around 300 nm, which corresponds to an energy gap of 4.13 eV. From the LIXPS and UPS results, the HOMO level is measured to be 7.2 eV below the vacuum level. Hence, the absorption results indicate a LUMO of 3.07 eV below the vacuum level. As explained below, the energy levels in the SAM can be used to draw an energy diagram across the Au|SAM|cyt c|RC to assess the limitations in the ET.

Figures 10A, 10B, 10C:
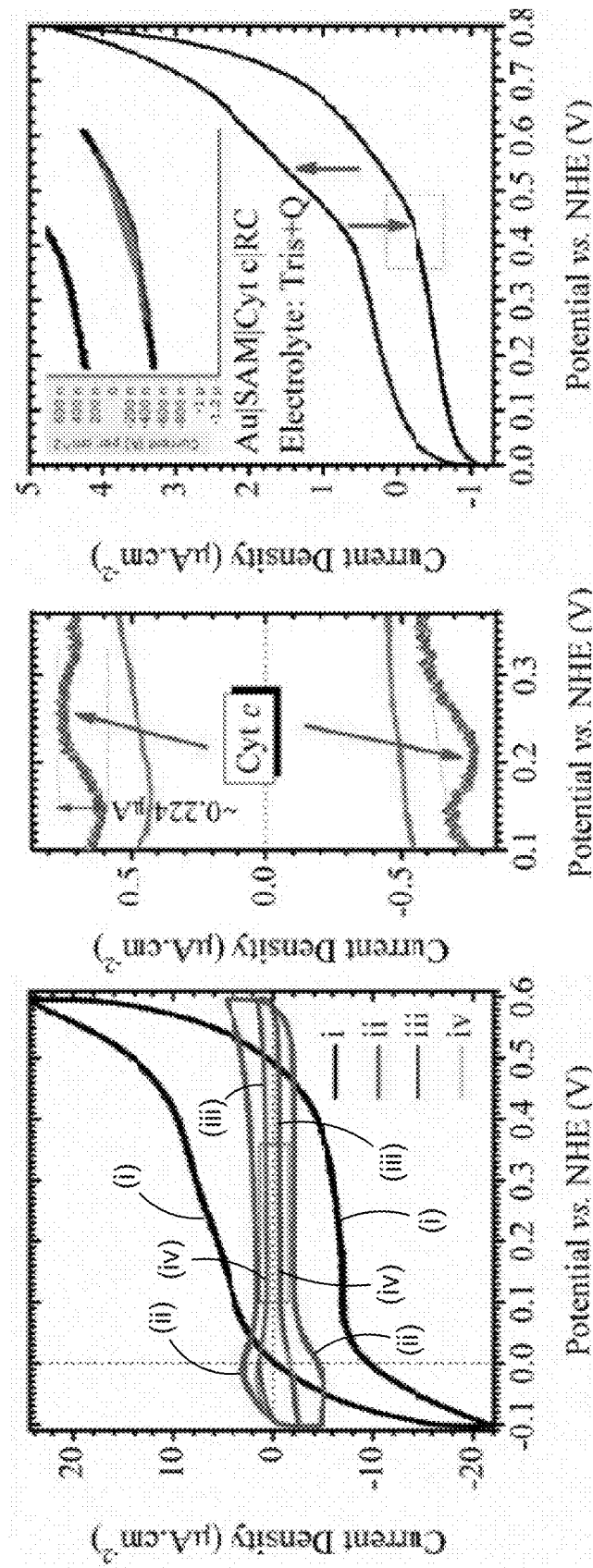
FIG. 10(a) is a graph that shows the cyclic voltammetries (CVs) of (i) an Au electrode; (ii) an Au|SAM electrode; (iii) Au|SAM|cyt c; and (iv) Au|SAM|cyt c|RC.
FIG. 10(b) is a close-up view of the horizontal rectangle in FIG. 10(a) and shows a pair of quasi-reversible redox peaks attributed to the heme Fe III/Fe II couple in cyt c, at approximately 0.23 V versus a normal hydrogen electrode (NHE).
FIG. 10(c) is a graph of the CV of the Au|SAM|cyt c|RC electrode (scan rate of 0.05 V·s$^{-1}$) in the presence of Q, which shows oxidation-reduction peaks of the RC primary donor (P). The inset shows the anodic peak scaled to emphasize the area of interest. The surface under the peak was used to estimate the density of immobilized RCs.

To estimate the electrochemical midpoint potentials (i.e. energy levels) and the surface coverage of the proteins, electrochemical cyclic voltammetry (CV) was performed for each layer. FIG. 10(a) shows the CVs of Au, Au|SAM, Au|SAM|cyt c, and Au|SAM|cyt c|RC electrodes at a scan rate of 0.05 V·s$^{-1}$ at room temperature. As curve ii of FIG. 10 shows, the Au electrode primed with a layer of 6-mercaptohexanoic acid exhibited no electroactivity in the potential range from 0.1 V to 0.6 V in the 0.1 M Tris-HCl (pH 8.0) background electrolyte. When the scan range was extended below 0.0 V versus NHE (i.e., the case here) the CV of the SAM showed a pair of peaks corresponding to protonation and de-protonation of the surface COOH groups.

After immobilization of cyt c, direct electrochemistry of surface-bound cyt c was achieved (FIG. 10, curve iii), and a pair of quasi-reversible redox peaks due to the one electron oxidation and reduction of a heme Fe III/Fe II couple was apparent at approximately 0.23 V versus NHE (FIG. 10(b)). The surface formal potential of cyt c is nearly identical to the values previously reported for cyt c bound to physiological membranes. From the average of the reduction and oxidation peak potentials, the redox potential of cyt c was measured to be approximately 0.23 V versus NHE (4.73 eV below vacuum level).

The CV result from RCs in the Au|SAM|cyt c|RC structure in the presence of quinone (Q) in the electrolyte is presented in FIG. 10(c). Because the immobilized proteins are present as a monolayer, the concentration of RC is very low and the redox peaks in the CV graph are relatively small. Nevertheless, the RC P peaks at ~0.4 V and 0.6 V versus NHE were observed, which confirms the RC immobilization. The midpoint potential of RC was estimated to be approximately +0.45 to 0.50 V (vs. NHE), which is similar to that reported in previous works. This confirms that in this structure the RCs are still redox-active upon docking to cyt c. As explained below, the area under the anodic peak (FIG. 10(b), inset) has been used to estimate the total amount of exchanged charges in the redox reaction of RCs from which the RC density and surface coverage were estimated.

The cathodic photocurrent in FIG. 4 indicates direction of ET from the Au electrode to the RC protein via the SAM|cyt c structure and accordingly confirms the anticipated protein orientation with the P-side facing the electrode. Although the photocurrent result shows the feasibility of immobilizing RCs through cyt c proteins, the overall photocurrent depends on the number of the immobilized RCs and the ET rate through the SAM|cyt c linker. Assuming a high degree of surface coverage by the SAM, the density of immobilized RCs is limited by the frequency of binding to cyt c. Using the results from the electrochemical experiments, an estimation of the surface coverage of the cyt c and the RC layers in described next. Also, the ET rate is estimated from the transient photocurrent response.

For surface coverage estimation of active cyt c heme proteins, the total charge was calculated by integrating the CV peak (FIG. 8(b)) after background subtraction. For Au|SAM|cyt c structures, the electroactive surface density of cyt c was determined by automatic CV peak integration, using VersaSTAT 4 software. Integrating the area under the peak of photocurrent density versus potential gives the charge density ($Q_{total}$). Using Faraday's Law, the electroactive surface concentration of cyt c can be then estimated using Eq. (2):

$$\Gamma = \frac{Q_{total}}{nF}, \qquad \text{Eq. (2)}$$

where $\Gamma$ is the electroactive surface density of cyt c, n is the number of unit charges in the redox reaction of the protein (n=1 in this case) and F is the faradaic constant (96485 C·mole$^{-1}$). Considering the surface area of the electrode, the surface density of approximately 14×10$^{-12}$ mole·cm$^{-2}$ was estimated for immobilized cyt c, which is consistent with a previous report. Considering the approximate diameter of a cyt c molecule, 3.3 nm, the calculated value of the cyt c surface concentration corresponds to an approximately 70% surface coverage of the electrode.

The CV peak integration technique was also applied to estimate the surface coverage of RC using the CV plot in FIG. 10(c). The measured charge density of approximately 581 nC (FIG. 10(c), inset) corresponds to a surface density of RC of 6.02×10$^{-12}$ mol·cm$^{-2}$. Considering the estimated density of cyt c on the surface (14×10$^{-12}$ mol·cm$^{-2}$) the number of attached RCs is almost half of the cyt c proteins on the electrode. Despite the lower number of RCs, based on the protein diameter (~5 nm) the RC surface coverage is estimated to be approximately 70%, which is in the same range as cyt c. Previous research has shown electrostatic interactions between acidic amino acids on the RC periplasmic surface (P-side) and the basic amino acid residues, primarily lysines, surrounding the cyt c heme contribute to inter-protein docking and stability of the RC-cyt c co-complex. Unpublished results show that R. sphaeroides cyt $c_2$ and horse heart cyt c are approximately 30% structurally similar. Additionally, cyt c was found to bind to the proximal position faster, as well as with a higher affinity of the oxidized form to the RC. In the current study, the photocurrent density of Au|SAM|cyt c|RC structure confirms the binding of cyt c and RC complexes. Additionally, the photocurrent direction proves that cyt c binds to the P-side of the RC protein complex. This binding configuration here can be compared to the mechanism known for the in vivo RC and cyt c proteins bond, as proposed by others.

Figure 11:
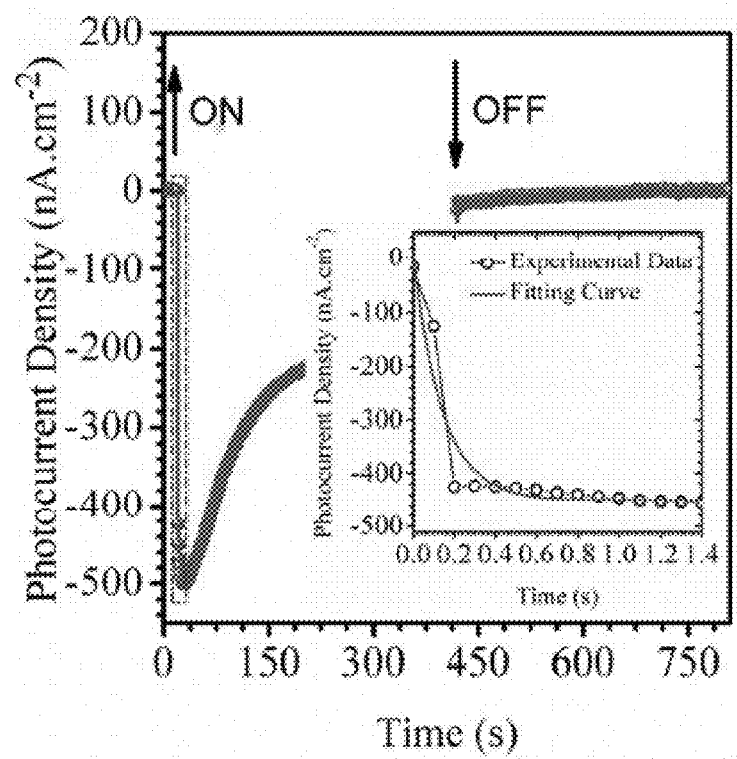
FIG. 11 is a graph of the photocurrent transition (inset, close-up view of the dashed rectangle) at the onset of illumination for Au|SAM|cyt c|RC electrode (onset of illumination at 0.0 s, and cessation of illumination as indicated by the upward and downward pointing arrows).

The ET rate between RC and the Au electrode in the Au|SAM|cyt c|RC structure was estimated through the photocurrent transition at the onset of illumination. FIG. 11 shows the photocurrent transition (1.4 s) for the RC-modified Au electrode with RC proteins sitting on cyt c-terminated SAMs. Assuming the transient photocurrent follows an exponential profile, the current density, J, was fitted to $J_{peak}(1-e^{-kt})$, where $J_{peak}=-450$ nA cm$^{-2}$ is the peak current density, k is the ET rate, and t is time (t=0 is the onset of the illumination). Based on the fitting curve in FIG. 11, the ET rate between the RC and the Au electrode was estimated to be k=7.1 s−1. The relatively low ET rate in the Au|SAM|cyt c|RC structure can be explained by an energy diagram of the different layers, shown in FIG. 12. The electrochemical midpoint potentials of the cyt c heme and P+ in RC were measured at 0.23 V and 0.45 V versus NHE, respectively (FIG. 10). The energy levels inside the RC have been studied in detail by others and explained by Blankenship. The midpoint potential of Q at pH 8 was measured in our earlier work as approximately 0.042 V versus NHE. The vacuum potential of Pt and the electrochemical potential of the QB site within the RC were also presented in a previous report. The HOMO and LUMO levels for the SAM were obtained from UPS, LIXPS, and UV-Vis absorption results (FIGS. 8 and 9).

Figure 12:
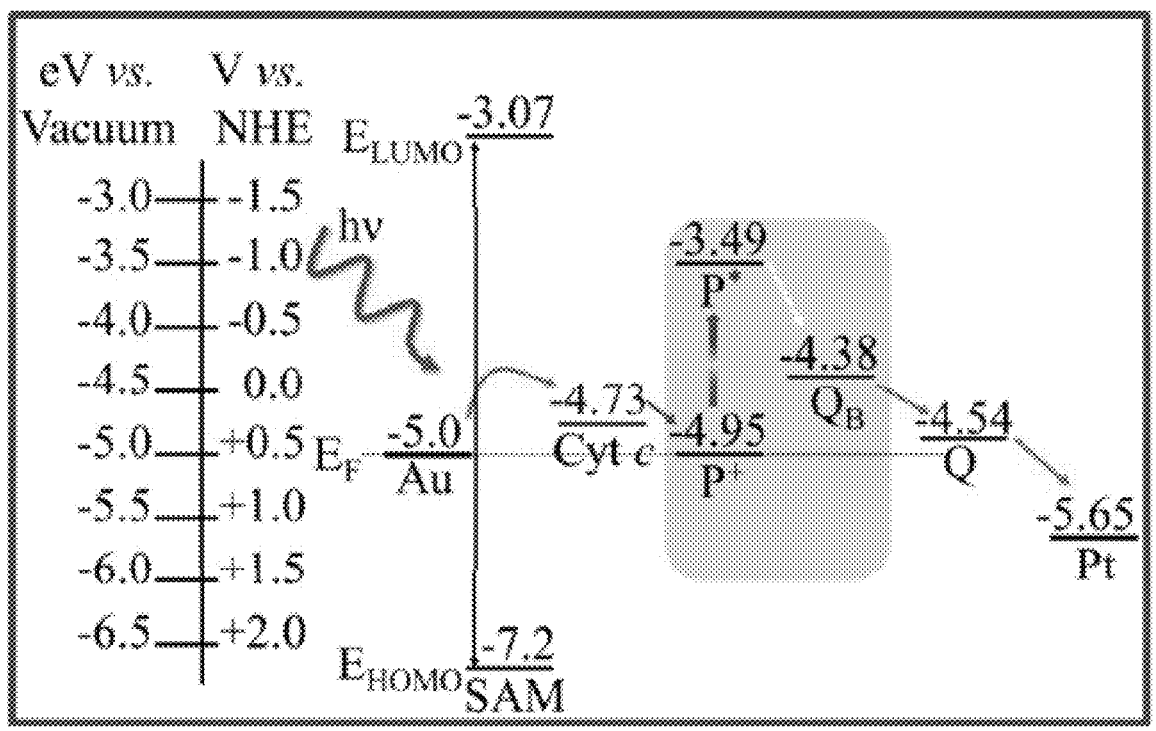
FIG. 12 is an energy diagram of the bio-electrochemical cell with the Au|SAM|cyt c|RC structure and the disclosed mechanism for operation of the cells with Q as the single diffusible redox mediator. RC complexes are modeled as oriented with the P-side toward the Au electrode. Arrows indicate the route of electron transfer (ET) from the Au to cyt c, into the P-side of the RC, and through Q to the Pt electrode. The energy level at each layer is relative to the vacuum level. The corresponding electrochemical potentials can be found from the normal hydrogen electrode (NHE) axis at the right.

The observed cathodic photocurrent implies ET from the Au to P+ in the RC while the energy diagram in FIG. 12 shows that the ET is hindered by the energy barrier of the SAM and the unfavorable energy difference between Au and cyt c. Although the Au Fermi level is below the cyt c energy level, the density of electrons above the Fermi level is not zero at room temperature. Additionally, WF measurement of the sputtered Au was performed in vacuum. The WF of a surface can be strongly affected by the condition of the surface. In the event of surface reactions (such as oxidation or reduction), the WF can change considerably. Hence, it is reasonable to assume that there are electrons with enough energy to tunnel through the SAM to the cyt c.

Figure 13:
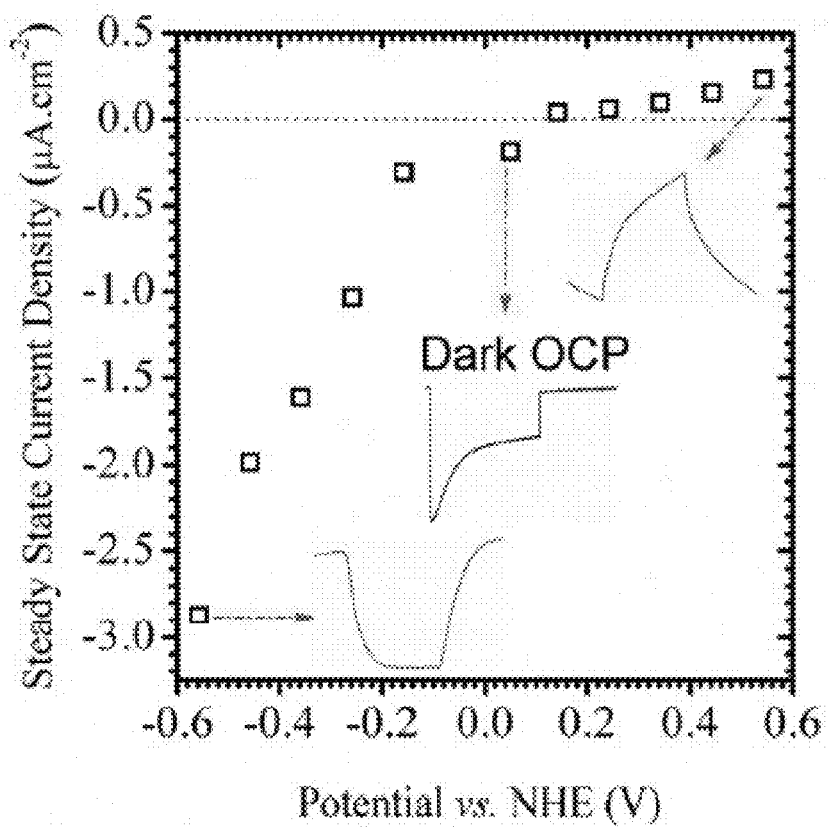
FIG. 13 is a graph of the effects of cycling the applied potential on the mean steady state current densities obtained from the Au|SAM|cyt CIRC electrode.

The effect of cycling the applied potential on the generated photocurrents was also examined to better understand the ET mechanism (FIG. 13). FIG. 13 demonstrates that, at applied potentials of −0.558 V to 0.050 V (vs. NHE), significant cathodic (negative) photocurrent densities were measured whereas at the applied potentials of 0.142 V to 0.542 V (vs. NHE), anodic (positive) photocurrent were recorded. The maximum photocurrent density of −2.872 µA cm$^{-2}$ was measured at the applied potential of −0.558 V versus NHE. The change in the photocurrent direction occurred around the applied potential of 0.142 V versus NHE. These observations correlate well with the proposed energy diagram and the operation mechanism for such cells in FIG. 12.

Considering the energy barrier ($\Delta E_1$) of 1.93 eV (the difference between $E_F$ (Au) and $E_{LUMO}$ (SAM)) and the tunneling length (a) of 3.0 nm (FIG. 6 sample 2—the distance from the electrode to the middle of cyt c where heme is located), the wave function for an electron tunneling through the SAM experiences attenuation. Using a simple square barrier model for the SAM, the one dimensional conductance, G, through the barrier can be found from Eq. (3):

$$G = \frac{2e^2}{h}T(\Delta E_2), \qquad \text{Eq. (3)}$$

where e=1.6×10$^{-19}$ C is the charge of one electron, h=6.626×10−34 J·s is Planck's constant, and T($\Delta E_2$) is the tunneling transmission coefficient between two energy states across the barrier with an energy difference of $\Delta E_2$. For a large barrier, the transmission coefficient is estimated by Eq. (4):

$$T(\Delta E_2) \approx \frac{16\Delta E_2}{\Delta E_1}\exp\left(-\frac{4\pi\sqrt{2m_e\Delta E_1}}{h}a\right), \qquad \text{Eq. (4)}$$

where $m_e$=9.11×10$^{-31}$ kg is the electron mass. From Eqns. (2) and (3), the one-dimensional conductance of the barrier is estimated to be G=4.65×10$^{-23}$|Ω$^{-1}$, which is very low. It should be noted that G is not the conductance of the SAM, but is the conductance along a single linker molecule (in one dimension). As shown in FIG. 4, the SAM has an important role in the protein immobilization since without the linker, no photocurrent was observed (mainly due to the cyt c adsorption orientation). In order to eliminate the charge transfer barrier, a conjugated linker molecule with a HOMO level slightly higher than the energy level in cyt c could be used. In this case, the ET would occur by the charge hopping through the hybrid conjugated molecule-cyt c linker, instead of tunneling. Additionally, a low WF material for the working electrode would greatly increase the ET rate.

The invention claimed is:

1. A method for immobilizing a target protein on an electrode, the method comprising:
   providing the electrode comprising a bare metal surface, wherein the bare metal surface is an outermost surface of the electrode;
   attaching a linker protein comprising cytochrome c to the bare metal surface of the electrode by directly attaching the linker protein comprising cytochrome c to the bare metal surface of the electrode; and
   directly attaching the target protein to the attached linker protein to immobilize the target protein relative to the bare metal surface of the electrode,
   wherein the target protein is only indirectly attached to the bare metal surface of the electrode via the linker protein.

2. The method of claim 1, wherein the electrode comprises gold, and
   wherein providing the electrode comprising the bare metal surface comprises:
   providing the electrode comprising a bare gold surface.

3. The method of claim 2, wherein attaching the cytochrome c to the bare metal surface of the electrode further comprises:
   attaching the cytochrome c to the bare gold surface of the electrode.

4. The method of claim 3, wherein the target protein is a photosynthetic reaction center protein, and
wherein directly attaching the target protein to the attached linker protein further comprises:
directly attaching the photosynthetic reaction center protein to the cytochrome c.

5. The method of claim 4, wherein the electrode is a working electrode, and
wherein the method further comprises:
providing a counter electrode adjacent to the working electrode,
exposing the photosynthetic reaction center protein to light, and
monitoring a photocurrent between the working electrode and the counter electrode based on exposing the photosynthetic reaction center protein to the light.

6. The method of claim 5, wherein providing the counter electrode adjacent to the working electrode further comprises:
providing the counter electrode adjacent to the working electrode in an electrolyte solution.

7. The method of claim 6, wherein providing the counter electrode adjacent to the working electrode in the electrolyte solution further comprises:
providing the counter electrode adjacent to the working electrode in the electrolyte solution comprising a charge carrier mediator comprising at least one of quinone or ferrocene.

8. A method for immobilizing a target protein on an electrode, the method comprising:
providing the electrode comprising a bare metal surface, wherein the bare metal surface is an outermost surface of the electrode;
attaching a linker protein comprising plastocyanin to the bare metal surface of the electrode by directly attaching the linker protein comprising plastocyanin to the bare metal surface of the electrode; and
directly attaching the target protein to the attached linker protein to immobilize the target protein relative to the bare metal surface of the electrode,
wherein the target protein is only indirectly attached to the bare metal surface of the electrode via the linker protein.

9. A method for immobilizing a target protein on an electrode, the method comprising:
providing the electrode comprising a bare metal surface, wherein the bare metal surface is an outermost surface of the electrode;
attaching a linker protein to the bare metal surface of the electrode by directly attaching the linker protein to the bare metal surface of the electrode; and
directly attaching the target protein to the attached linker protein to immobilize the target protein relative to the bare metal surface of the electrode,
wherein the target protein is only indirectly attached to the bare metal surface of the electrode via the linker protein, and
wherein directly attaching the target protein to the attached linker protein further comprises:
directly attaching at least one of *R. sphaeroides* bacterium RC, *R. sphaeroides* bacterium RCLH1 +Pufx, *R. sphaeroides* bacterium RC-LH1 −Pufx, a Photosystem I protein, a Photosystem II protein, a protein complex from the phycobilisome protein family, or a bacteriorhodopsin protein to the attached linker protein.

* * * * *